US 7,626,166 B2

(12) United States Patent
Saito et al.

(10) Patent No.: US 7,626,166 B2
(45) Date of Patent: Dec. 1, 2009

(54) ELECTRON MICROSCOPE

(75) Inventors: Hiroyuki Saito, Hitachinaka (JP); Katsuhiro Sasada, Hitachinaka (JP)

(73) Assignee: Hitachi High-Technologies Corporation, Tokyo (JP)

(*) Notice: Subject to any disclaimer, the term of this patent is extended or adjusted under 35 U.S.C. 154(b) by 81 days.

(21) Appl. No.: 12/038,076

(22) Filed: Feb. 27, 2008

(65) Prior Publication Data

US 2008/0203301 A1 Aug. 28, 2008

(30) Foreign Application Priority Data

Feb. 28, 2007 (JP) ............................. 2007-049930

(51) Int. Cl.
*H01J 37/16* (2006.01)
*H01J 3/14* (2006.01)
*G01N 23/04* (2006.01)

(52) U.S. Cl. .................... 250/311; 250/310; 250/307; 250/306

(58) Field of Classification Search ................ 250/306, 250/307, 310, 311, 396 R, 396 ML, 441.11
See application file for complete search history.

(56) References Cited

U.S. PATENT DOCUMENTS 6,956,211 B2 * 10/2005 Sato et al. ....................... 850/1

2004/0119022 A1 * 6/2004 Sato et al. ................ 250/396 R
2008/0203301 A1 * 8/2008 Saito et al. ................... 250/311

FOREIGN PATENT DOCUMENTS

| JP | 359181448 A | * | 10/1984 |
| JP | 11-135052 A | | 5/1999 |
| JP | 2006-093161 A | | 4/2006 |
| JP | 2006-140070 A | | 6/2006 |
| JP | 2008-218015 | * | 9/2008 |

* cited by examiner

*Primary Examiner*—Bernard E Souw
(74) *Attorney, Agent, or Firm*—Crowell & Moring LLP

(57) ABSTRACT

An object of the present invention is to prevent foreign bodies attracted by a magnetic field of an objective lens or an electric field of an electrode plate and adhered to a surface of the objective lens or electrode plate from dropping onto the surface of a sample and adhering there during observation of the sample.

To achieve the above object, an electron microscope in which, when a sample to be measured is moved away from below an objective lens, an exciting current to the objective lens of a scanning electron microscope is turned off or excitation thereof is made weaker than before the sample to be measured being moved away, or an applied voltage to an acceleration cylinder for accelerating an electron beam is turned off or made lower than before the sample to be measured being moved away is proposed.

6 Claims, 5 Drawing Sheets

1···PRIMARY ELECTRON BEAM  2,3···SECONDARY ELECTRONS  4···CATHODE
5···CONDENSER LENS  6···OBJECTIVE LENS  7···SCANNING DEFLECTOR
8···SAMPLE (WAFER)  9···SAMPLE STAGE  10···CONVERSION ELECTRODE
11···SECONDARY ELECTRON DETECTOR

30···LOAD LOCK CHAMBER  31···VACUUM SAMPLE CHAMBER
32···GATE VALVE

40⋯ACCELERATION CYLINDER

ELECTRON MICROSCOPE

BACKGROUND OF THE INVENTION

1. Field of the Invention

The present invention relates to a scanning electron microscope for semiconductor inspection that detects a scanning image of a sample (semiconductor wafer) by detecting secondary electrons emitted from the sample by irradiation of electron beams (primary electron beams), and in particular, relates to an electron microscope that reduces an influence of foreign bodies attached to the sample.

2. Description of the Related Art

In a scanning electron microscope for semiconductor inspection, an operation of carrying a sample into a vacuum sample chamber and, after the sample being observed, of carrying the sample out of the vacuum sample chamber is performed. An objective lens is excited to cause electron beams to be focused on a sample during observation of the sample and, when observation of the sample is completed, an operation of carrying in the next non-inspected sample is performed. Since an excited state of the objective lens is maintained at this time, the electron microscope is always used in a state in which a magnetic field is generated in the objective lens. The electron microscope is frequently used in a low acceleration voltage area and a technology described in Japanese Patent Application Laid-Open No. 2006-93161 is available as a means for increasing resolution also in the low acceleration voltage area. That is, an electrode is provided in an objective lens part and resolution of secondary electron images is increased by applying a positive high voltage to the electrode. Also in this case, an electric field is applied during observation of the sample and when the sample is carried in and carried out, and the electron microscope is always used while an electric field is generated.

As circuit patterns formed on a semiconductor wafer become increasingly more microscopic and complex, on the other hand, management of foreign bodies of microscopic size has become a big problem because foreign bodies of more microscopic size adhering to the sample surface during observation of the sample seriously affect semiconductor elements.

Factors of microscopic foreign bodies generated in an apparatus of an electron microscope include, in addition to rubbing and abrasion of a sample transfer system mechanism, foreign bodies adhering to the sample surface being carried into the apparatus. Such microscopic foreign bodies are always exposed to a magnetic field of the excited objective lens and a strong electric field by a high voltage applied to the electrode.

For the purpose of reducing foreign bodies generated inside the apparatus, components worn out in the transfer system mechanism are wiped off with a dustproof cloth, cleaned using a lubricant, or replaced. A method disclosed in Japanese Patent Application Laid-Open No. 2006-140070 is known as a method of more actively removing foreign bodies adhering to the surface of a sample. A foreign body removing apparatus disclosed in Japanese Patent Application Laid-Open No. 2006-140070 removes foreign bodies by providing a nozzle-shaped structure in a sample replacement apparatus and injecting a high-pressure gas such as nitrogen toward the surface of a sample.

Japanese Patent Application Laid-Open No. 11-135052 describes, in a scanning electron microscope equipped with a secondary electron detector and an X-ray detector, using an objective lens by switching excitation conditions in order to perform an X-ray analysis without losing a target observation visual field after making a high-resolution observation of a sample.

In a conventional electron microscope, an objective lens is excited for observation of a sample to cause electron beams (primary electron beams) to be focused on the sample and, after observation of the sample, the sample is carried out and the next non-inspected sample is carried in while the excited state of the objective lens is maintained. Since, at this time, a magnetic field generated by an objective lens and a strong electric field generated by an electrode plate act on microscopic foreign bodies adhering to the surface of the sample, a force of attraction acts on such foreign bodies, leading to adhesion to the objective lens and the electrode plate. Then, foreign bodies adhering to the objective lens and the electrode plate accumulate and, when a certain amount is exceeded, such foreign bodies drop onto the surface of the sample and re-adhere as foreign bodies, posing a problem.

As described above, components worn out in a transfer system mechanism are cleaned or replaced as countermeasures to reduce foreign bodies from the viewpoint of preventive maintenance. However, this method requires stopping operation of the apparatus for a long time to perform cleaning or component replacement, creating a problem of a reduced working ratio of the apparatus. Moreover, foreign bodies generated unexpectedly cannot be dealt with and therefore, work will realistically continue in most cases with foreign bodies, posing a new problem.

According to a technique disclosed in Japanese Patent Application Laid-Open No. 2006-140070, a nozzle-shaped structure is provided in a sample replacement chamber and a high-pressure gas such as nitrogen is injected toward the surface of a sample immediately before observation of the sample to remove foreign bodies adhering to the surface of the sample and constituting an obstacle to sample observation by blowing off such foreign bodies. However, there are problems that arrangement of the nozzle-shaped structure between an objective lens of the sample replacement chamber of an electron microscope and a sample is structurally complex and difficult and the degree of vacuum in the sample chamber falls after injecting a gas sufficiently to blow off foreign bodies and thus, a time is needed to increase the degree of vacuum again.

The distance between an objective lens and a sample in a recent electron microscope actually measuring patterns whose dimensions are below 90 nm is only several mm or so, and it is extremely difficult to arrange a nozzle and a pipe for connecting the nozzle in this area. In addition, in order to blow off foreign bodies whose size is 100 nm or larger, a viscous flow of at least several tens to 100 Pa is needed, instead of a molecular flow, but if the degree of vacuum is lowered to such an extent, it becomes difficult for the electron microscope to observe secondary electron images. Thus, after removing foreign bodies by nozzle injecting, it is necessary to exhaust air up to a vacuum region ($10^{-2}$ to $10^{-3}$ Pa) required for observation of SEM images (secondary electron images).

Further, a technology disclosed by Japanese Patent Application Laid-Open No. 11-135052 does not refer to removal of foreign bodies at all.

An object of the present invention is to provide an apparatus that reduces an influence of foreign bodies to allow stable sample observation by preventing foreign bodies attracted to a magnetic field of an objective lens or an electric field of an electrode plate and adhering to the surface of the object lens or the electrode plate from dropping onto the surface of a sample and adhering to the sample during observation of the sample and to provide an apparatus that allows stable sample observation without reducing a working ratio or throughput of the apparatus.

SUMMARY OF THE INVENTION

To achieve the above objects, in an aspect of the present invention, an electron microscope in which, when a sample to be measured is moved away from below an objective lens, an exciting current to the objective lens of a scanning electron microscope is turned off or excitation thereof is made weaker than before the sample to be measured being moved away, or an applied voltage to an acceleration cylinder for accelerating an electron beam is turned off or made lower than before the sample to be measured being moved away is proposed. Since foreign bodies can be caused to drop while there is no sample below the objective lens, stable measurement and inspection can be made without foreign bodies being dropped onto the sample.

According to the configuration described above, foreign bodies that could adhere to the surface of a sample can effectively be removed and therefore, stable measurement and inspection can be made.

DESCRIPTION OF THE PREFERRED EMBODIMENTS

Figure 1:
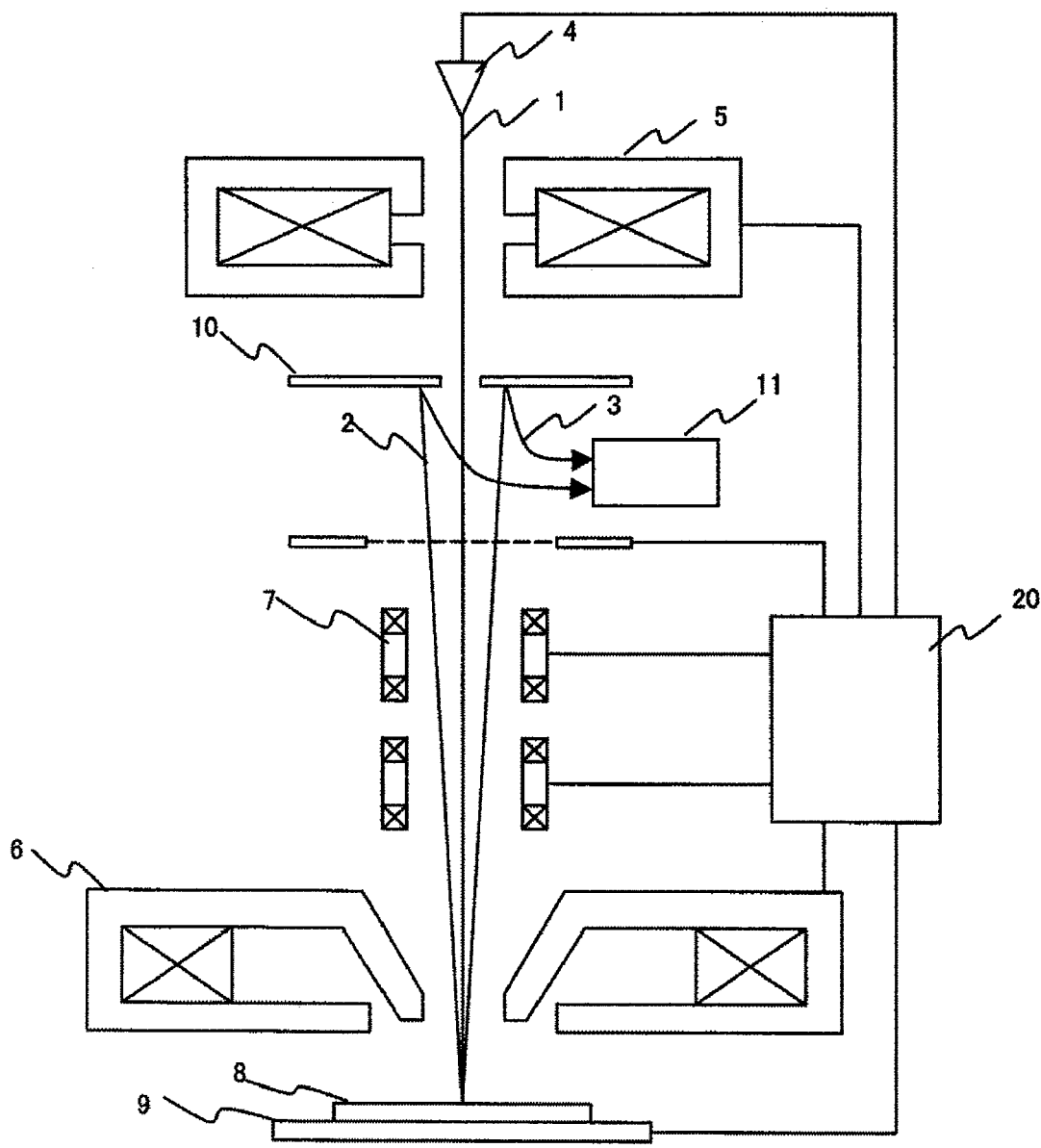
FIG. 1 is a diagram illustrating an overview of a scanning electron microscope.

In embodiments described below, in an electron microscope having an electron source generating electron beams, a condenser lens for focusing electron beams, an objective lens for irradiating a sample with electron beams by narrowing them down, a deflector for two-dimensionally scanning electron beams on the sample, and a secondary signal detector for detecting secondary signals generated by irradiation of the sample with electron beams, an example of a scanning electron microscope that includes a control device capable of controlling an excited state of the objective lens, controls excitation of the objective lens so that an SEM image can be observed by focusing electron beams on the sample through the objective lens during observation of the sample, and controls excitation of the objective lens so that excitation of the objective lens is turned off or the excited state thereof is made weaker than that during observation of the sample when the sample is not observed.

According to an example of such a scanning electron microscope, foreign bodies adhering to the objective lens can be caused to drop when there is no sample immediately below by turning off excitation of the objective lens or making the excited state thereof weaker when the sample is carried out after observation of the sample is completed even if foreign bodies adhere to the objective lens during observation of the sample and therefore, adhesion of foreign bodies to the sample can be prevented. Foreign bodies attracted by a magnetic field of the objective lens are metallic foreign bodies having magnetism and this aspect is effective when stainless foreign bodies containing large amounts of Fe (iron), Ni (nickel), and Co (cobalt) frequently used particularly for transfer systems are generated.

In another aspect of a scanning electron microscope, in the above electron microscope in which a means for applying a positive voltage accelerating primary electron beams to an acceleration cylinder arranged on an electron beam path of an objective lens and a means for applying a negative voltage to a sample are provided, an electric field for decelerating primary electron beams is formed between the acceleration cylinder and the sample, and a secondary signal detector is arranged at a position on the side of the electron source from the acceleration cylinder, a means for exercising control such that the electric field formed between the acceleration cylinder and the sample is turned off or made weaker than during observation of the sample in synchronization with controlling excitation of the objective lens by the control device or asynchronously is provided.

Accordingly, foreign bodies adhering to the electrode plate can be caused to drop when there is no sample immediately below by turning off an applied voltage to the electrode plate or making the excited state thereof weaker when the sample is carried out after observation of the sample is completed even if foreign bodies adhere to the electrode plate during observation of the sample and therefore, adhesion of foreign bodies to the sample can be prevented. This is effective for insulating or non-conductive foreign bodies that cause electrification on the surface thereof to be attracted by an electric field and particularly for organic material and resinous material.

According to an aspect of the present invention described above, foreign bodies adhering to an objective lens can be prevented from dropping onto the surface of a sample and adhering there during observation of the sample by controlling excitation of the objective lens in a scanning electron microscope for semiconductor inspection and therefore, an effect of mitigating the foreign body problem is gained so that an apparatus that can make stable sample observation can be provided.

According to another aspect of the present invention, an effect of being able to operate an apparatus without lowering throughput can be gained by synchronizing timing of excitation control of an objective lens with opening/closing of a gate valve for sample transfer and therefore, a highly productive and stable apparatus can be provided.

Embodiments of the present invention will be described below with reference to drawings.

First Embodiment

FIG. 1 shows a first embodiment of a scanning electron microscope for semiconductor inspection of the present invention. A primary electron beam 1 derived from a cathode 4, which is a portion of an electron source, is narrowed down by a condenser lens 5 and further two-dimensionally scanned by a scanning deflector 7 on a wafer 8. The primary electron beam 1 is decelerated by a retarding electric field between an objective lens 6 and the wafer 8 under the influence of a negative retarding voltage applied to the wafer via a sample stage 9 and thinly narrowed down on the wafer by a lens action of the objective lens 6.

When the primary electron beam 1 is irradiated on the wafer 8, secondary electrons 2 are generated. Since the electric field created between the objective lens 6 and the wafer 8 acts as an accelerating electric field on the generated secondary electrons 2, the secondary electrons 2 are attracted into an electron beam passing hole of the objective lens 6 and go up under the lens action by a magnetic field of the objective lens 6. The secondary electrons 2 that have gone up collide against conversion electrodes 10 with high energy to newly generate secondary electrons 3. The secondary electrons 3 are attracted by a scintillator of a secondary electron detector 11 to which a high voltage of about 10 kV of the anode is applied and collide against the scintillator, giving off light when the collision occurs. The light, which is not shown, is converted into an electric signal and, after being amplified, brightness of a cathode-ray tube is controlled by output thereof.

A control device 20 controls the above-described cathode 4, condenser lens 5, objective lens 6, scanning deflector 7, and secondary electron detector 11, and sets optimal optical conditions (such as the cathode voltage, condenser lens current value, objective lens current value, deflection control signal, and secondary electron detector control voltage) for observation of a sample. FIG. 1 has been described by assuming that the control device 20 is integrated with the electron microscope or in an equivalent configuration, but the present embodiment is not necessarily limited to this and processing may be performed from a control device provided separately from the electron microscope body. In this case, a transfer medium for transferring detection signals detected by the secondary electron detector to a control processor and transferring signals from the control processor to the lens or deflector of the electron microscope, and an input/output terminal for inputting/outputting signals transferred via the transfer medium is needed. Alternatively, a control program for performing processing may be registered in a storage medium to execute the program from the control device having an image memory and equipped with a means for supplying signals necessary for the electron microscope.

A coil is wound inside the objective lens 6 and a magnetic field lens is formed in the objective lens by passing a current to the coil via the control device 20. Here, intensity of the magnetic field lens can be changed by changing the amount of current passed to the coil.

Figure 2:
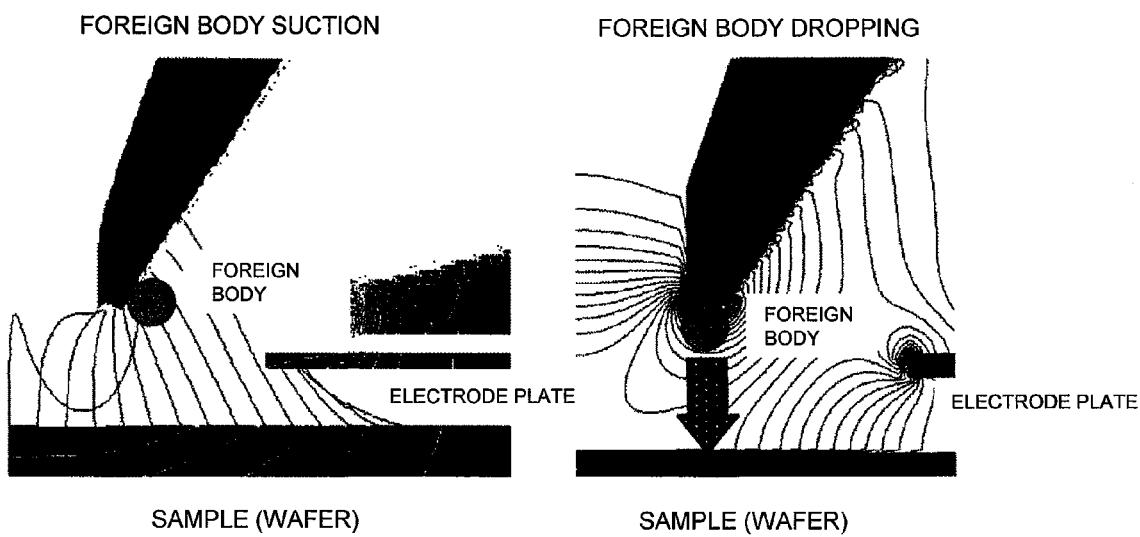
FIG. 2 is a diagram illustrating a mechanism of suction, dropping, and adhesion of foreign bodies.

Minimum pattern dimensions of the current semiconductor process are below 100 nm and are expected to reach microscopic dimensions of several tens nm. Insulation materials are frequently used in materials used for semiconductor circuits and an accelerating voltage of several hundreds to 800 V is used for observation of SEM images. Since resolution of 2 nm or less is required as performance of an electron microscope for observation of microscopic patterns of several tens nm, a working distance of the objective lens of 2 to 3 mm or less is needed and a magnetic field will necessarily act on the sample. FIG. 2 shows enlarged views near the objective lens and, if a foreign body having magnetism of the size of 100 nm or so exists on the sample, an upward force of attraction acts on the foreign body due to a magnetic field of the objective lens and, if the force of attraction exceeds the sum of the mass of the foreign body and an adhesive force to the sample surface, the foreign body is attracted toward the objective lens before being adhered to the surface of the objective lens. When secondary electrons generated by irradiation of the sample with the electron beam collide against the foreign bodies, the foreign bodies are charged positively and repel the objective lens, which has a positive voltage, and drop before being adhered to the surface of the sample. If observation is repeated extending over a certain period, the number of foreign bodies in the sample chamber gradually increases and also the number of foreign bodies adhering to the surface of the sample inevitably increases.

In the example shown in FIG. 1, the amount of current passed to the coil of the objective lens 6 is lowered or blocked by the control device 20 to make the magnetic field of the objective lens 6 weaker or turn off the magnetic field after observation of the wafer 8 is completed and the sample stage 9 carries the wafer 8 out of the vacuum sample chamber. Foreign bodies are prevented from dropping onto the surface of the sample and adhering there during observation of the sample by causing the foreign bodies adhering to the objective lens 6 in advance before observation of the sample by turning off excitation of the objective lens 6 or making excitation thereof weaker than during observation of the sample when no sample is observed.

Since foreign bodies may drop onto a sample if excitation is turned off before a wafer to be measured is carried out of the sample chamber, it is preferable to control the excited state of the objective lens after confirming that the sample has been carried out of the sample chamber. However, if foreign body removal processing should be performed at high speed, excitation may be turned off after the wafer moves out of a region below magnetic poles of the objective lens (in the example of FIG. 2, an interval specified between a tip of an upper magnetic pole of the objective lens and the electrode plate in a direction of the sample surface), which is an assumed area of foreign body dropping.

Since there is a possibility that dropped foreign bodies are brought back if excitation is turned on immediately after dropping the foreign bodies to restore the excited state, it is desirable to restore the excited state after a predetermined time elapses or the sample stage is moved.

The foreign body removal process may be performed at each predetermined timing or when a detection result of a foreign body detection apparatus set up separately exceeds a predetermined value. Alternatively, the foreign body removal process may be performed each time when a predetermined number of wafers is processed. The control device 20 performs foreign body removal (turning off an exciting current of the objective lens or weaker excitation) based on a trigger issued based on the time, the number of wafers, and/or the foreign body detection apparatus.

Second Embodiment

Figure 3:
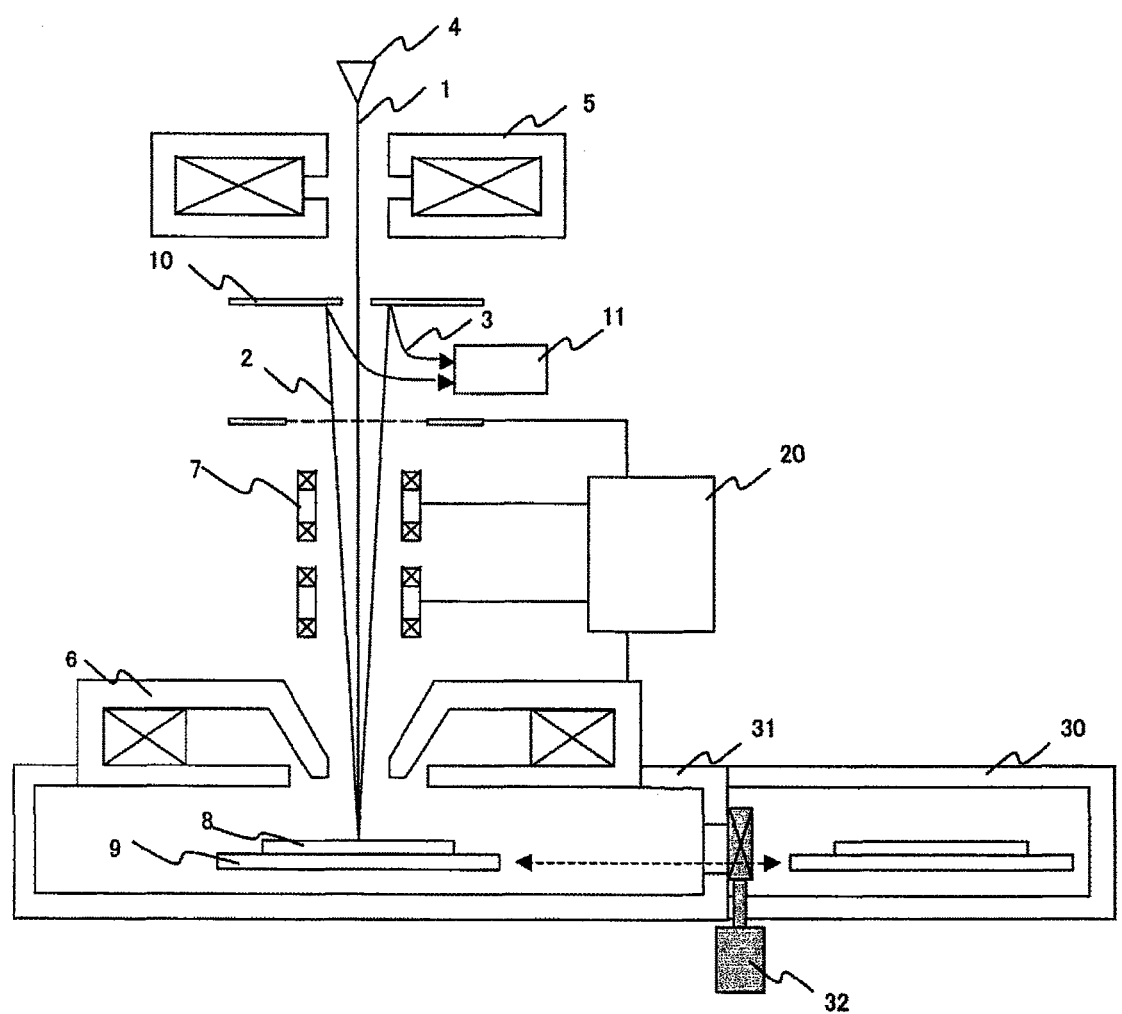
FIG. 3 is a diagram illustrating the overview of a scanning electron microscope equipped with a load lock chamber.

FIG. 3 shows a second embodiment and, in addition to the first embodiment shown in FIG. 1, a load lock chamber 30, which is a preliminary vacuum chamber of sample, and the sample stage 9 for carrying wafers are provided and a vacuum sample chamber 31 and the load lock chamber 30 are adjacent to each other via a gate valve 32.

A series of operation of excitation control (ON/OFF switching) of an objective lens according to the present invention will be described. It is assumed that a predetermined degree of vacuum is maintained inside the vacuum sample chamber 31.

The wafer 8 is carried into the load lock chamber 30 by a transfer robot (not shown). At this point, the inside of the load lock chamber 30 is under atmospheric pressure and air is exhausted until a predetermined degree of vacuum is reached. After air is exhausted from the load lock chamber 30 up to the predetermined degree of vacuum, the gate valve 32 between the load lock chamber 30 and the vacuum sample chamber 31 is opened. Simultaneously with the opening of the gate valve 32, excitation of the objective lens is turned off or the excited state thereof is made weaker than during observation of the sample to cause foreign bodies adhering to the objective lens to drop in advance before starting observation of the sample. Then, the wafer 8 is transferred on the sample stage 9 arranged in the vacuum sample chamber 31. Then, the gate valve 32 is closed. Simultaneously with the closing of the gate valve 32, excitation of the objective lens is turned on and the wafer 8 is observed by the electron microscope while the sample stage 9 moves inside the vacuum sample chamber 31.

In the present embodiment, an influence of foreign bodies adhering to the surface of an objective lens can be reduced by turning off excitation of the objective lens or making an excited state thereof weaker in synchronization with opening/closing of the gate valve without affecting the processing time of a transfer sequence.

Third Embodiment

Figure 4:
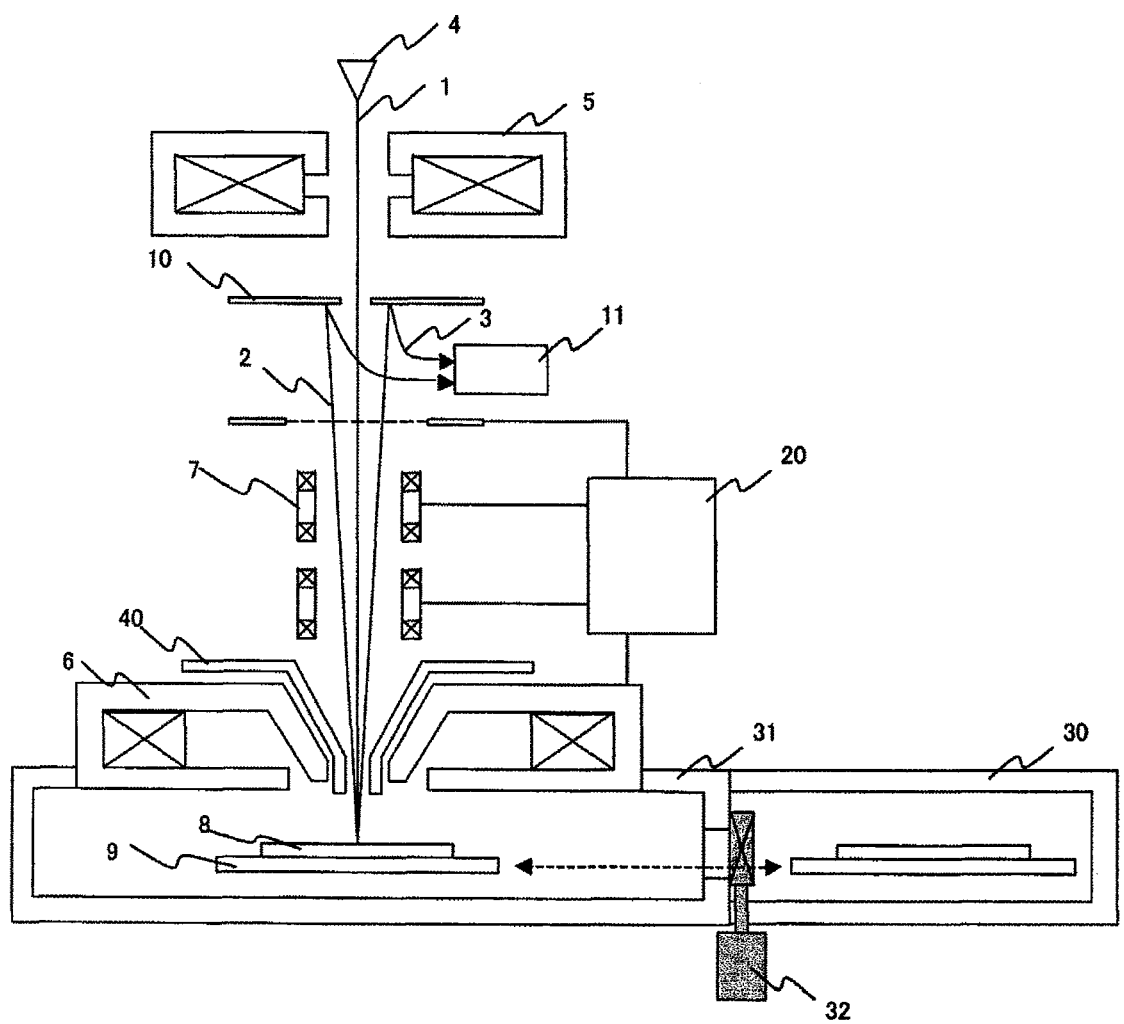
FIG. 4 is a diagram illustrating the overview of a scanning electron microscope equipped with an acceleration cylinder.

FIG. 4 shows a third embodiment, and a acceleration cylinder 40 is arranged on an electron beam path of the objective lens 6 and a positive voltage accelerating the primary electron beam 1 is applied to the arranged acceleration cylinder 40 to form an electric field decelerating the primary electron beam 1 between the acceleration cylinder 40 and the wafer 8. Since an accelerating voltage of the primary electron beam 1 when passing through the objective lens 6 can thereby be made higher than a final accelerating voltage, blurring of the beam due to aberration generated in the objective lens 6 can be decreased so that a scanning image with high spatial resolution in a low acceleration voltage area can be obtained. If an upper electrode determining the lens center of the objective lens 6 and the acceleration cylinder 40, which is an electrode plate, are combined, there is no deviation between an electrostatic lens and a magnetic lens and therefore, there are advantages that the lens center position of the electrostatic lens and that of the magnetic lens can be matched and also the lenses can be controlled easily with a non-complex electron optics system. However, a strong electric field acts on a sample if a positive potential of about +5 V is applied to the acceleration cylinder and, if charged foreign bodies exist on the surface of the sample, a problem arises that the foreign bodies adhere to the surface of the electrode at the tip of the acceleration cylinder 40 after being attracted by the strong electric field.

In the present embodiment, foreign bodies adhering to the surface of the electrode plate of the acceleration cylinder 40 due to an electric field can be removed for cleaning by turning off the electric field formed between the acceleration cylinder 40 and the wafer 8 or making the electric field state weaker (lower voltage) than during observation of the sample in synchronization with timing of excitation control (ON/OFF switching) of the objective lens 6 and therefore, a problem of foreign bodies adhering to the surface of the sample can be prevented.

Fourth Embodiment

As another embodiment of the present invention, if the above work is done repeatedly, the number of foreign bodies generated inside the vacuum sample chamber 31 is expected to increase as the number of times of work increases and, for example, periodic cleaning inside the vacuum sample chamber 31 is performed by carrying in a specific sample after observing several wafers. In contrast to work in the aforementioned first embodiment, excitation of the objective lens 6 is turned off or an excited state thereof is made weaker than during normal observation of the sample for observation of the sample only when the specific sample is carried in so that foreign bodies that have adhered to the objective lens 6 during preceding observation are intentionally caused to drop onto the sample surface and to adhere there. Accordingly, foreign bodies that have been generated can be cleaned and an influence of foreign bodies can be reduced and therefore, stable sample observation can be made during the next observation.

Figure 5:
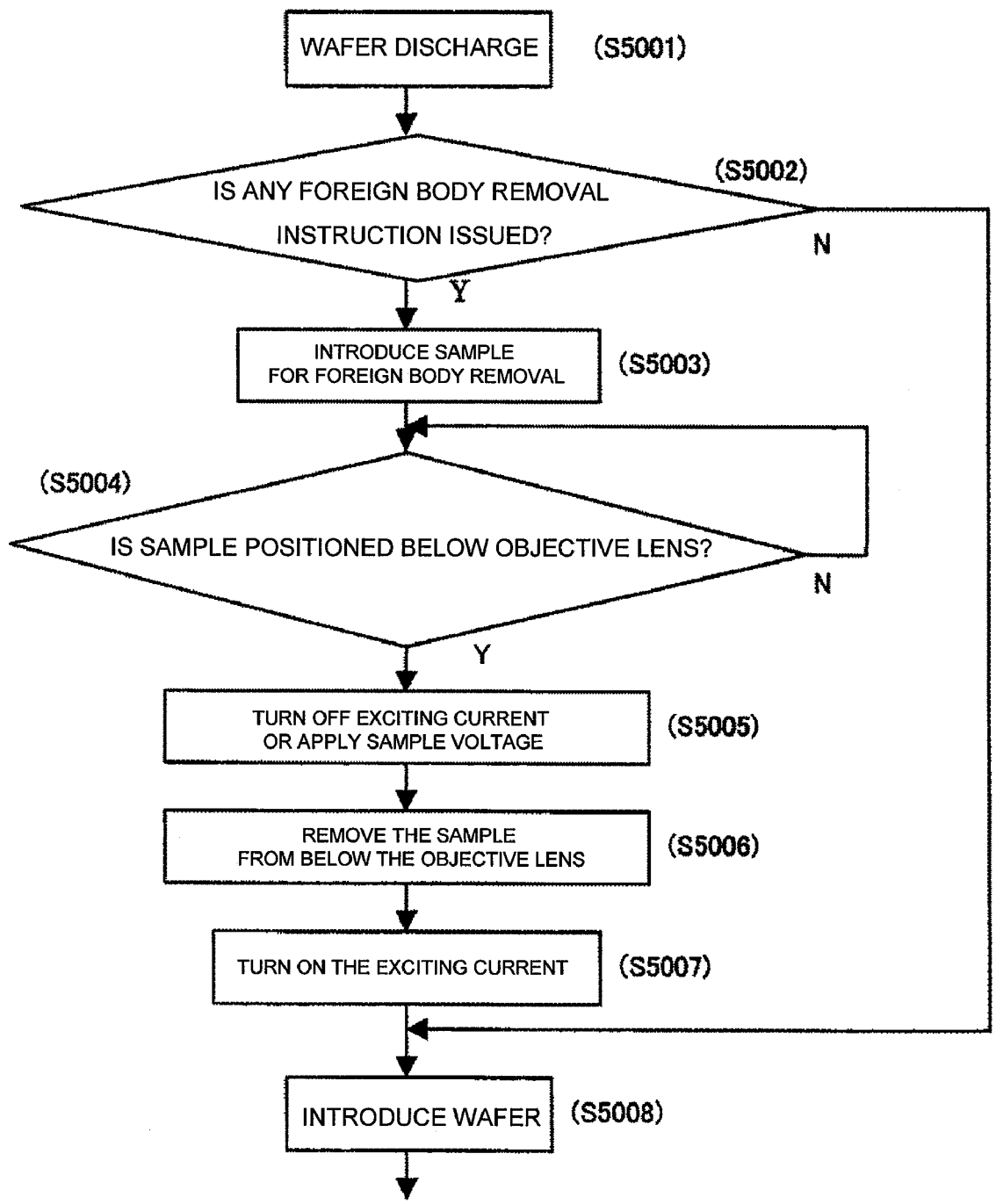
FIG. 5 is a flow chart showing a procedure for foreign body removal processing.

A concrete example thereof will be described using a flow chart in FIG. 5. FIG. 5 is the flow chart showing a procedure for removing foreign bodies using a sample for removing foreign bodies.

Particularly in an apparatus for making semiconductor measurements or inspections, samples are automatically measured or inspected continuously based on an operation program of the apparatus called a recipe. Such an apparatus is required to reduce a down time to a minimum. To shorten a time needed for removing foreign bodies in such an apparatus, it is preferable to include a foreign body removal process in the normal measurement or inspection process. FIG. 5 shows the flow chart showing the procedure for removing foreign bodies using, for this purpose, a sample for removing foreign bodies.

After a sample measured or inspected is discharged from a sample chamber (S5001), the control device 20 determines whether any foreign body removal instruction has been issued based on recipe setting or the like (S5002). If no instruction has been issued, the next sample to be measured or inspected is carried into the sample chamber (S5008).

However, if a foreign body removal instruction has been issued, a sample for foreign body removal is carried into the sample chamber (S5003). Then, after confirming that the sample for foreign body removal is positioned below the objective lens (S5004), control is exercised so that an exciting current of the objective lens is turned off or excitation thereof is made weaker (S5005). The weaker excitation here refers to a current weaker than an exciting current usually used for focusing an electron beam on a sample and is weaker than an exciting current used for scanning on a sample using an electron beam.

Further, in S5004, foreign bodies that have dropped on the sample for foreign body removal are caused to be adsorbed electrostatically by turning on an applied voltage to the sample. With a configuration in which foreign bodies are not only caused to drop, but also maintained firmly on the sample, secondary scattering of foreign bodies inside the sample chamber can effectively be controlled.

In the present example, foreign bodies adhering to the objective lens and the like can effectively be removed by setting an apparatus state in which the applied voltage to the sample is turned on while excitation of the objective lens is turned off or made weaker, which is different from a normal condition of use of an electron microscope.

Moreover, whether a sample is a conductor or an insulator, foreign bodies can be maintained on the sample by an operation of electrostatic induction or dielectric polarization. The scanning electron microscope described in the present example adopts a retarding technology in which energy of electron beams reaching the sample is retarded by applying a negative voltage to the sample. The retarding technology is a technology to realize both high resolution by maintaining energy of electron beams when passing through the objective lens at a high level and reduced damage by reducing energy reaching the sample, and in the present example, the retarding technology is applied also to foreign body removal.

Incidentally, the retarding technology is used in the present example to adsorb foreign bodies onto the sample for foreign body removal, but the technology is not limited to this and, it is also possible to prevent foreign bodies from dropping into the sample chamber by causing a sample itself, which is equipped, for example, with a function to generate an electrostatic adsorption force or the like, to generate an adsorption force when a current of the objective lens is turned off or excitation thereof is made weaker.

Further, if the sample for foreign body removal has the same shape as that of a semiconductor wafer, the sample for foreign body removal can be carried into the sample chamber using the same transfer mechanism used for the semiconductor wafer. If the sample for foreign body removal does not have the same size as that of the semiconductor wafer, it is preferable to reduce the size of the sample in view of flexibility of movement in the vacuum chamber. However, from a functional viewpoint of receiving dropping foreign bodies, the sample preferably has a larger diameter than a portion where foreign bodies adhere (for example, an upper magnetic pole of the objective lens).

Though it is possible to prevent foreign bodies from dropping onto a sample by causing foreign bodies to drop while the sample is removed from the sample stage without using the sample for foreign body removal, it is preferable to remove foreign bodies by using the sample for foreign body removal from the viewpoint of exhaustively removing foreign bodies from within the sample chamber.

Here, after foreign body removal, it is necessary to turn on an exciting current of the objective lens while the sample for foreign body removal is away from below the objective lens. If the exciting current of the objective lens is turned on while the sample remains below the objective lens, foreign bodies may re-adhere. Thus, it is necessary to turn on the exciting current of the objective lens after the sample is moved away such a distance that a focusing magnetic field of the objective lens does not reach the place where foreign bodies dropped. For this purpose, for example, restoring the exciting current when the sample is discharged from the sample chamber can be considered. However, if the apparatus should be started more swiftly, the exciting current may be restored when the sample is a predetermined distance away from the objective lens while moving between the sample chamber and the load lock chamber.

In order at least not to cause foreign bodies to re-adhere to the objective lens, it is preferable to turn on the exciting current of the objective lens when the place where foreign bodies dropped leaves an area under the influence of a leakage magnetic field of the objective lens. It is preferable to turn on the exciting current at least after the sample area (the place where foreign bodies dropped) immediately below the magnetic pole of the objective lens moves away from below the magnetic pole of the objective lens.

A foreign body removal instruction is set, for example, at each predetermined time, after a predetermined number of sample measurements, or according to an optional instruction. Based on such instructions, the control device 20 performs processing such as turning off an exciting current of the objective lens. In order to increase operating efficiency, the apparatus is configured in such a way that applying states of currents and voltages to each component are maintained as long as no foreign body removal instruction is issued or no instruction to turn off an exciting current of something else is issued.

In order to increase operating efficiency of a scanning electron microscope making measurement or inspection of semiconductor patterns, the apparatus always or for a long period of time continues to operate. Some of such apparatuses are configured so that measurement or inspection can immediately be started when a sample is introduced into the sample chamber by maintaining excitation of the objective lens in a predetermined state even when no sample is introduced in the sample chamber. For such apparatuses, the above example in which selectively the exciting current is turned off or excitation thereof is made weaker is very effective for removing foreign bodies, and suitable cleaning can be performed while maintaining operating efficiency of the apparatus at a high level.

Incidentally, the exciting current when excitation of the objective lens is made weaker is a value smaller than that for normal measurement or inspection. The objective lens can be adjusted within a variable range of the exciting current in accordance with normal measurement conditions and the like, but by setting the exciting current to a value still lower than the range, foreign bodies are caused to drop.

Turning off excitation conditions (exciting current) of the objective lens or making excitation thereof weaker has been described above, but the present invention is not limited to this and the applied voltage may be turned off or lowered to remove foreign bodies on other electrodes or magnetic paths that could adsorb foreign bodies.

Alternatively, foreign bodies may be caused to drop by turning off the exciting current of the objective lens and the applied voltage to the acceleration cylinder together or lowering the exciting current and the applied voltage.

DESCRIPTIONS OF REFERENCE NUMERALS

1: Primary electron beam
2, 3: Secondary electrons
4: Cathode
5: Condenser lens
6: Objective lens
7: Scanning deflector
8: Sample (wafer)
9: Sample stage
10: Conversion electrode
11: Secondary electron detector
20: Control device
30: Load lock chamber
31: Vacuum sample chamber
32: Gate valve
40: Acceleration cylinder

What is claimed is:

1. An electron microscope comprising an electron source, an objective lens for focusing an electron beam emitted from the electron source, and a control device for controlling an exciting current of said objective lens, wherein said control device controls said exciting current so that the exciting current of said objective lens is turned off or excitation thereof is made weaker than during scanning of a sample to be measured when said sample to be measured by said electron beam is at least moved away from below said objective lens.

2. The electron microscope according to claim 1, wherein said control device exercises control to turn off the exciting current of said objective lens or to make excitation thereof weaker at each predetermined time and/or after a predetermined number of samples.

3. The electron microscope according to claim 1, wherein when a predetermined number of foreign bodies is detected, said control device exercises control to turn off the exciting current of said objective lens or to make excitation thereof weaker.

4. The electron microscope according to claim 1, comprising a vacuum chamber in which a sample irradiated with said focused electron beam is arranged, a load lock chamber for preliminarily exhausting air from sample space when the sample is introduced into the vacuum chamber, and a gate valve arranged between the vacuum chamber and the load lock chamber, wherein said control device exercises control to turn off the exciting current of said objective lens or to make excitation thereof weaker simultaneously with opening of said gate valve.

5. The electron microscope according to claim 1, comprising an acceleration cylinder for accelerating said electron beam when passing through said objective lens, wherein said control device exercises control so that a voltage applied to said acceleration cylinder is turned off or made lower than during scanning of said sample to be measured when the exciting current of said objective lens is turned off or excitation thereof is made weaker.

6. A sample measuring method of measuring a sample using an electron beam by scanning the electron beam focused on the sample by using an objective lens, wherein foreign bodies adhering to a portion of said objective lens are caused to drop by turning off an exciting current of said objective lens or excitation thereof is made weaker when said sample moves away from below said objective lens and below a portion of said objective lens where foreign bodies adhere when said objective lens is excited.

* * * * *